United States Patent [19]
Widlund et al.

[11] Patent Number: 6,152,907
[45] Date of Patent: *Nov. 28, 2000

[54] ABSORBENT ARTICLE

[75] Inventors: Urban Widlund, Mölnlycke; Anders Gustafsson, Billdal; Anna Svernlöv, Kullavik, all of Sweden

[73] Assignee: Molnlycke AB, Gothenburg, Sweden

[ * ] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 09/070,751
[22] Filed: May 1, 1998

Related U.S. Application Data

[62] Division of application No. 08/704,705, Sep. 10, 1996.

[30] Foreign Application Priority Data

Mar. 18, 1994 [SE] Sweden .................................. 9400916

[51] Int. Cl.$^7$ ...................................................... A61F 13/15
[52] U.S. Cl. ................................ 604/385.08; 604/385.19; 604/385.24; 604/385.25; 604/385.26; 604/385.27; 604/385.28
[58] Field of Search ........................... 604/317, 327–331, 604/346–358, 369, 374–378, 385.1, 385.2, 397–399; 128/98.1; 602/67

[56] References Cited

U.S. PATENT DOCUMENTS

| | | |
|---|---|---|
| 3,424,160 | 1/1969 | Koornwinder et al. . |
| 3,532,093 | 10/1970 | Lovret . |
| 4,490,148 | 12/1984 | Beckestrom . |
| 4,662,877 | 5/1987 | Williams . |
| 4,695,278 | 9/1987 | Lawson . |
| 4,704,116 | 11/1987 | Enloe . |
| 4,738,677 | 4/1988 | Foreman . |
| 4,935,021 | 6/1990 | Huffman et al. . |
| 5,171,236 | 12/1992 | Dreier et al. . |

FOREIGN PATENT DOCUMENTS

| | | |
|---|---|---|
| 0 486 006 | 5/1992 | European Pat. Off. . |
| 0 581 044 | 2/1994 | European Pat. Off. . |
| 2-84623 | 7/1990 | Japan . |
| 3-121069 | 5/1991 | Japan . |
| 3-123553 | 5/1991 | Japan . |
| 9202817-9 | 1/1994 | Portugal . |
| 2 022 026 | 11/1991 | Spain . |
| 1 298 527 | 12/1972 | United Kingdom . |
| 2 268 073 | 1/1994 | United Kingdom . |

OTHER PUBLICATIONS

Opposition to EP–13–0748199, Oct. 29, 1995.
Ruling regarding 19963807, Jan. 8, 1996.
Translation of Spanish patent No. 2, 022,026, Apr. 1998.
Translation of Portuguese 9202817.

*Primary Examiner*—Aaron J. Lewis
*Assistant Examiner*—K. M. Reichle
*Attorney, Agent, or Firm*—Young & Thompson

[57] ABSTRACT

An absorbent article having a front part (12), a rear part (14) and an intermediate crotch part (13), such as a diaper, an incontinence guard or like article. The article includes an absorbent body (1), a liquid-impermeable bottom sheet (7) joined to the absorbent body, and a top sheet (9) which is free from connection with the absorbent body over a large part of its surface and which lies proximal to the wearer's body when the article is worn, and which top sheet includes an opening (15) which extends from the rear article part into the crotch part, and elastic devices (24, 25) which are fastened to the top sheet in a stretched state and which when contracting from the stretched state cause the part of the top sheet that is not joined to the absorbent body to be distanced from the body. The top sheet (9) includes a further opening (16) which extends from the front part (12) into the crotch part (13). A piece (26) of flexible material extends transversely across the article between the absorbent body (1) and the top sheet (9) within that region of the top sheet that lies between the two openings (15, 16), this piece of flexible material being fastened to the absorbent body and to the top sheet.

10 Claims, 3 Drawing Sheets

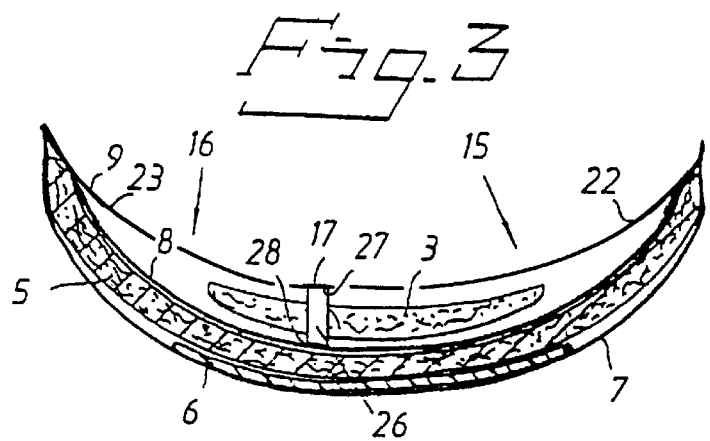
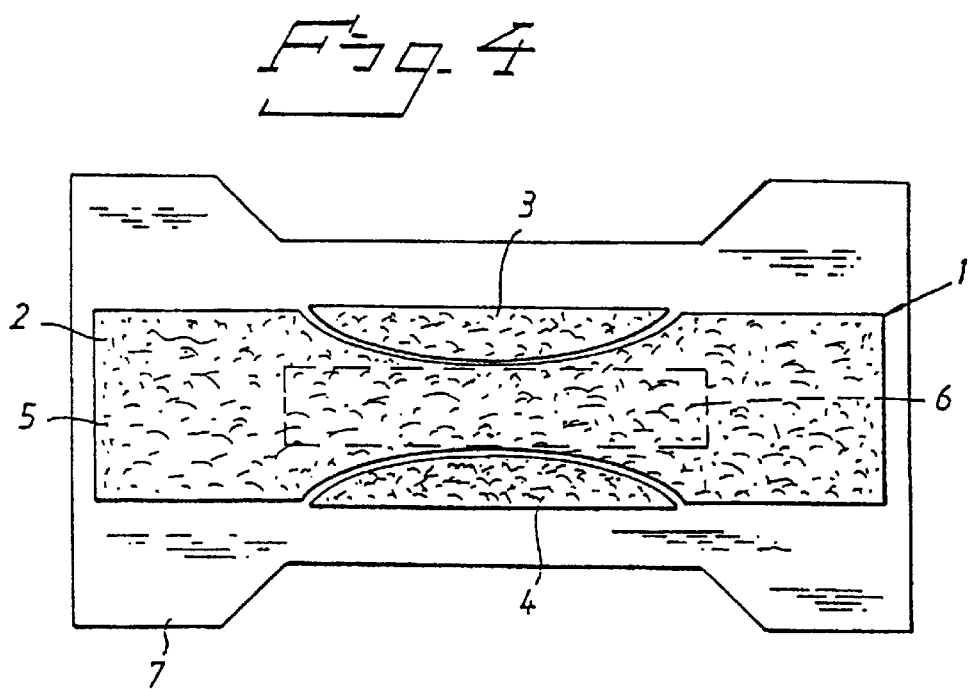
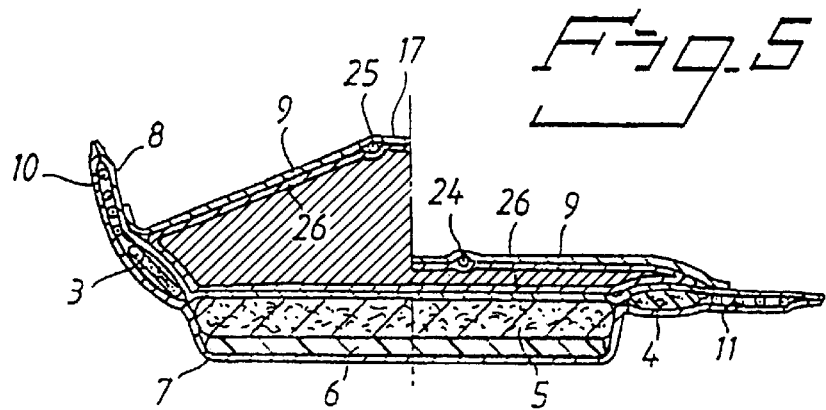

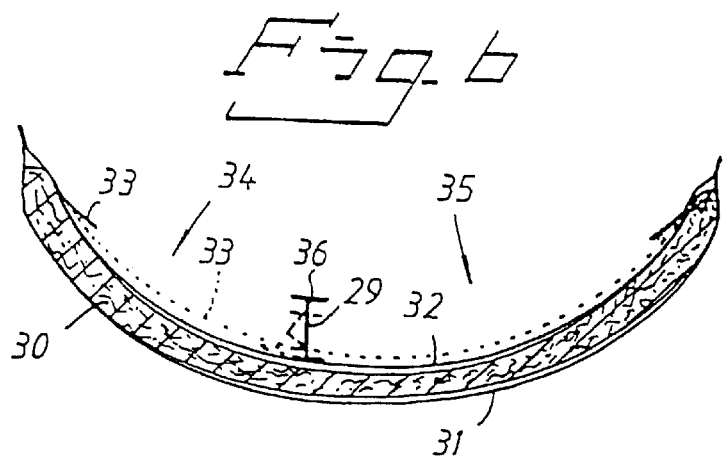

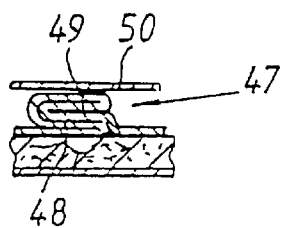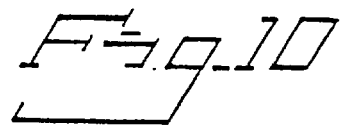

ABSORBENT ARTICLE

CROSS-REFERENCE TO RELATED APPLICATIONS

This application is a division of copending application Ser. No. 08/704,705, filed Sep. 10, 1996.

BACKGROUND OF THE INVENTION

The present invention relates to an absorbent article which has a front part, a rear part and an intermediate crotch part, such as a diaper, an incontinence guard or like article, which includes an absorbent body, a bottom sheet comprised of liquid-impermeable material and joined to the absorbent body, and a top sheet which over a large part of its surface is free from connection with the absorbent body, i.e. not directly joined thereto, and which when the article is worn lies proximal to the wearer's skin, said top sheet including an elongated opening which extends from the rear article part into the crotch part, and elastic devices which are attached to the top sheet in a stretched state and which when contracting from their stretched state cause that part of the top sheet which is not joined to the absorbent body to be distanced from absorbant body.

Diapers which are provided with an opening in the top sheet are known from AU-A-45217/85, EP-A2-0,357,298 and EP-A2-0,486,006 and are intended to avoid irritation of the wearer's skin as a result of excrement coming into contact with the skin. According to these publications, this is achieved because the absorbent body is brought to a basinlike shape as the elastic devices provided in the top sheet contract, at the same time as the top sheet is therewith distanced from the bottom of the basin to form a basin lid or cover which includes an opening. One problem with diapers of this kind is that the opening provided in the top sheet must be sufficiently large and so positioned as to ensure that excrement will fall safely from the wearer down onto the absorbent body. Any excrement that lands on the top sheet is highly liable to result in leakage and irritation of the skin. It has also been found that the skin is much more sensitive to a mixture of urine and faeces, and consequently it is important to minimize the risk of such a mixture coming into contact with the wearer's skin while the article is worn. When urine and faeces mix, ammonia is formed which leads to an increase in pH and also in greater activity of the faecal enzymes.

SUMMARY OF THE INVENTION

An object of the present invention is to ensure that urine and faeces will fall safely onto the absorbent body, and to prevent the urine and faeces discharged onto the absorbent body from mixing together. This object is achieved in accordance with the invention with an absorbent article of the kind defined in the introduction which is characterized in that the top sheet also includes a second elongated opening which extends from the front article part and into the crotch part, and in that a piece of flexible material extends transversely across the article between the absorbent body and the top sheet and within that area of the top sheet which lies between the two elongated openings, said piece of material being attached to the absorbent body and the top sheet. The provision of a front opening in the top sheet ensures that urine discharged from the wearer will fall onto the absorbent body, and the flexible piece of material forms a barrier which prevents urine from falling or running down over that part of the absorbent body onto which faeces are discharged and also to prevent faeces from entering that part of the absorbent body onto which urine is discharged. In addition to preventing urine and faeces mixing together, the arrangement also prevents faeces from coming into contact with the wearer's genitals.

According to one preferred embodiment of the invention, the absorbent body includes a liquid-permeable casing sheet on that side thereof which lies distal from the bottom sheet, and that area of the top sheet which lies between the two elongated openings is located between the wetting point and the faecal discharge point. The side edges of the two elongated openings diverge from the transverse edges in the crotch part, and the elastic devices in the top sheet extend along the side edges of the openings, and the material piece mounted transversely between the top sheet and the inner casing sheet of the absorbent body is comprised of a tubular body or member which is connected to the inner casing sheet and the top sheet transversely over a narrow region. The tubular body is advantageously formed integral with the top sheet.

More particularly, the absorbent article includes front and rear parts and a crotch part therebetween, an absorbent body extended longitudinally from the front part to the rear part, and a liquid-impermeable bottom sheet and a liquid-permeable casing sheet sandwiching the absorbent body A monolithic top sheet that lays proximal to a wearer's body when the article is being worn has a first opening therethrough at the front part and a second opening therethrough at the rear part, the openings each having longitudinal edges and respective front and rear part lateral edges spaced from peripheral edges of the top sheet and crotch part lateral edges separated from each other by a laterally extended bridge of the top sheet. The longitudinal edges of each of the openings converge continuously from a respective one of the front and rear part lateral edges to a respective one of the crotch part lateral edges to provide each of the openings with a truncated triangular shape when the top sheet is flat, such as shown in FIG. 2. The top sheet is directly connected to the casing sheet at a periphery of the top sheet. Elastic devices are fastened to the top sheet in the stretched state and separate the top sheet from the casing sheet when contracted, except at the periphery of the top sheet. A laterally aligned flexible member is connected to the top sheet across the bridge and is either directly connected to or is part of the casing sheet adjacent to the crotch part. The flexible member is a side of a first pouch that opens at the first opening and a side of a second pouch that opens at the second opening and separates the pouches from each other.

BRIEF DESCRIPTION OF THE DRAWINGS

The invention will now be described in more detail with reference to the accompanying drawings, in which

FIG. 3 is a schematic longitudinal sectional view of the diaper shown in FIG. 1, omitting portions of the casing sheet 8 on the side body 3 in the interest of clarity;

FIG. 4 is a view corresponding to the view of FIG. 2 aid illustrates the bottom sheet and the absorbent body of the diaper shown in FIG. 1;

FIG. 5 is a cross-sectional view taken on the line V—V in FIG. 2;

FIG. 6 is a longitudinal sectional view corresponding to the sectional view of FIG. 3 and illustrates a second embodiment of an inventive diaper; and FIGS. 7–10 illustrate various variants of the material pieces suitable for use in an inventive diaper.

DESCRIPTION OF PREFERRED EMBODIMENTS

Figure 1:
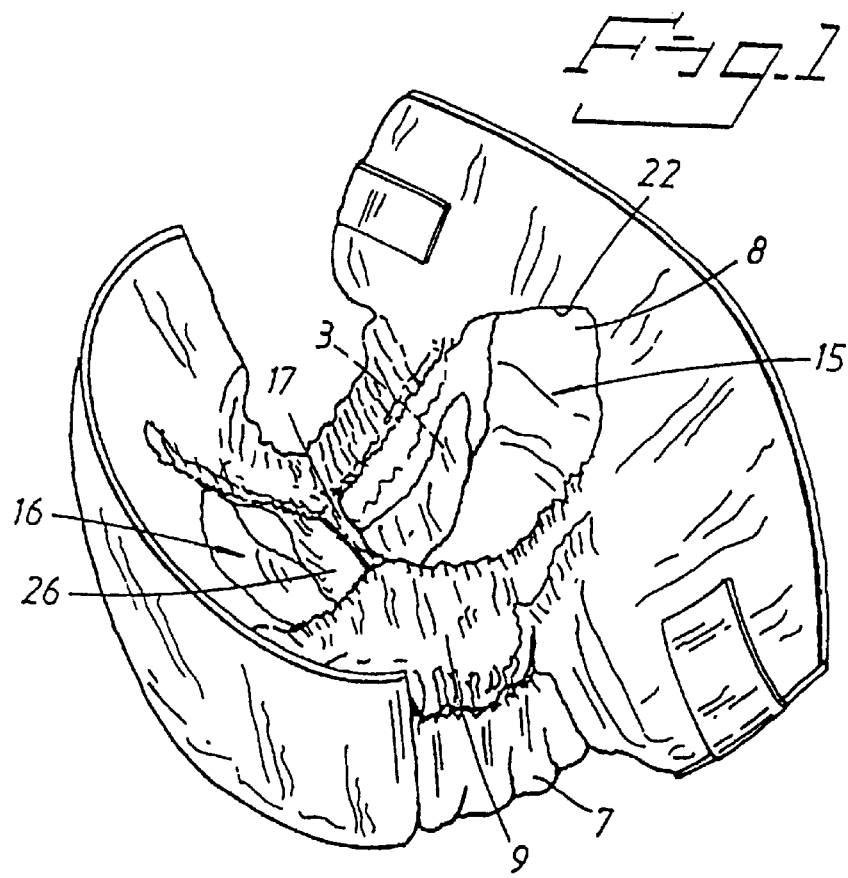
FIG. 1 is a schematic perspective view of one embodiment of an inventive diaper, taken obliquely from above.

The diaper illustrated in FIGS. 1–5 includes an absorbent body 1 which in the case of the illustrated embodiment is comprised of an hourglass-shaped main body 2 and two side bodies 3, 4. The main body 2 is comprised of two sheets 5, 6. The upper sheet 5 and the side bodies 3, 4 are comprised of air-laid cellulose fluff. The bottom sheet 6 is preferably comprised of air-laid cellulose fibres and is preferably compressed more heavily than the upper sheet 5. Alternatively, the bottom sheet 6 may be comprised of absorbent reel material of the type described in Swedish Patent Application No. 9203445-3, which includes a dry-formed sheet containing 5–100% cellulose fibres and has a density of between 0.2–1.0 g/cm$^3$ and a surface weight of between 30–2,000 g/m$^2$ and which has been formed by compressing a cellulose-fibre containing web without subsequent defibration and fluff building. The reader is referred to the aforesaid patent application for a closer study of this type of reel material. As will be seen from FIG. 4, the sheet 6 is rectangular in shape and extends beneath only a part of the sheet 5.

The absorbent body 1 is enclosed between an outer casing sheet or bottom sheet 7 of liquid-impermeable material, for instance polyethylene plastic, and an inner liquid-permeable casing sheet 8, which is preferably made of nonwoven material. The sheet 8 is preferably similar to the bottom sheet 7 and the sheets are joined together at parts which lie outside the absorbent body 1. As will best be seen from FIG. 4, the side bodies 3, 4 are located laterally slightly beyond the main body 2, and the casing sheets 7, 8 are joined together in the gap presented between the main body and the side bodies.

Figure 2:
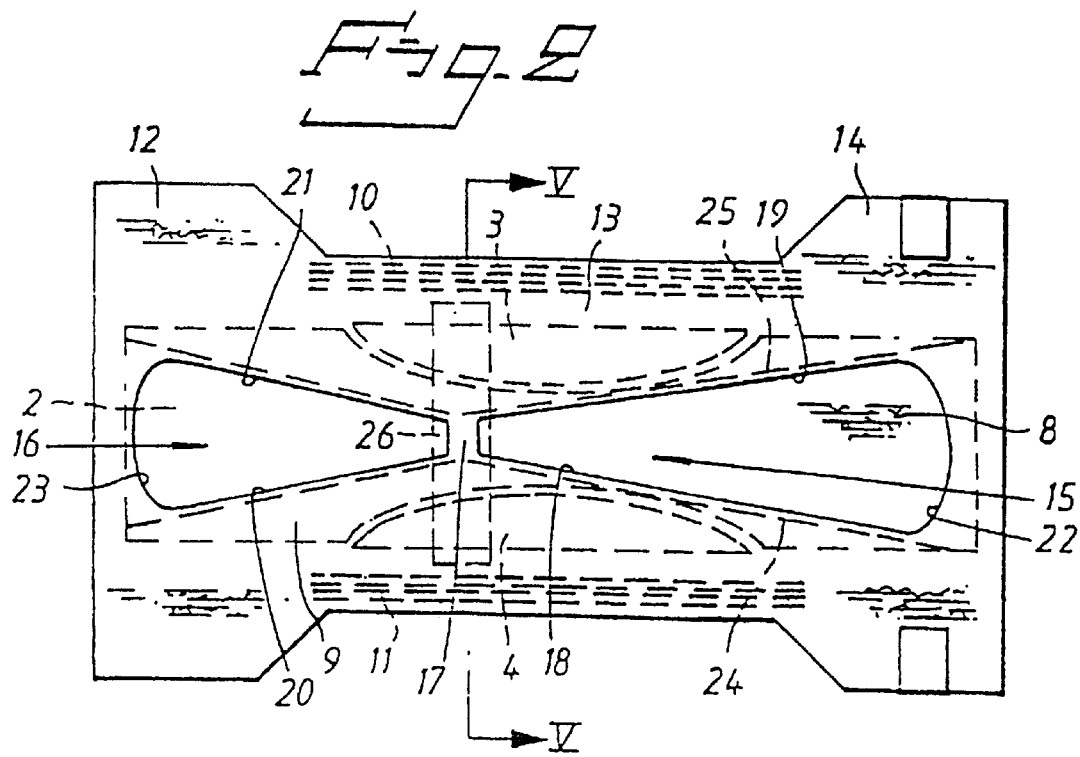
FIG. 2 is a schematic illustration of the diaper shown in FIG. 1 taken from above with the diaper in a flat state.

The diaper also includes a top sheet 9 which is similar to the casing sheets 7, 8 and is fastened thereto along diaper edge parts, so that the top sheet over a large part of its surface will be free from direct connection with the absorbent body 1, so that the top sheet can be distanced from the absorbant body as will be explained below. The top sheet is made from a skin-friendly material and may either be liquid-impermeable or liquid-permeable. As shown in FIGS. 1 and 2, the diaper is provided with leg elastication in the form of elastic devices 10, 11 which extend along the side edges in the crotch part 13 and in parts of the front diaper part 12 and the back diaper part 14. In the illustrated case, the elastic devices are comprised of four elastic threads which have been attached in a stretched state between the bottom sheet 7 and the inner casing sheet 8 and fastened to said sheets. It will be understood, however, that the elastic threads may be more or fewer in number and that other types of elastic devices may be used, such as elastic ribbon, film strips having elastic properties, etc. It will also be understood that the elastic devices 10, 11 may instead be placed between the top sheet 9 and the inner casing sheet 8.

The top sheet 9 includes two symmetrical openings, a rear opening 15 and a front opening 16, which are elongated in the longitudinal direction of the diaper. That region 17 of the top sheet 9 which lies between the openings 15, 16 in the longitudinal direction of the diaper is located between the wetting point and the faecal discharge point. By wetting point is meant that area of the diaper within which urine can be expected to be discharged when the diaper is correctly positioned on the wearer, while by faecal discharge point is meant correspondingly that region within which faeces are expected to be deposited when the diaper is positioned correctly, i.e. those regions which lie opposite the urethral orifice and the anus of the wearer respectively, while taking into account normal variations in the anatomy of the wearer within the wearer's size range for which the diaper is dimensioned. The side edges 18, 19 and 20, 21 of respective openings 15 and 16 diverge respectively forwardly and rearwardly from the top sheet region 17, and the openings have arcuate transverse edges 22, 23 which extend slightly from the rear and front end of the absorbent body.

Two elastic threads 24, 25 are attached in a stretched state to the top sheet 9 and extend from the front part of the front diaper part 12 to the rear part of the rear diaper part 14. The threads 24, 25 extend convergently towards one another from the front diaper part 12 to the region 17 of the top sheet 9, along the side edges 20, 21 of the opening 16, and then extend along the side edges 19 of the opening 15 roughly to the level of the rear edge 22 of the opening 15. In the illustrated embodiment, the threads 24, 25 are attached between the top sheet and narrow nonwoven strips (not shown) which are secured to the threads and to the top sheet by gluing or in some other suitable way. In the illustrated embodiment, the strips are positioned along the full length of the threads and the threads are therewith secured to the top sheet along their full lengths. This is not absolutely necessary, however, since the desired function can be achieved by fastening the threads to the top sheet at their respective ends and at the region 17.

According to one variant, the nonwoven strips are secured to the top sheet along their edges, so as to form elastic-thread guide passages. In this case, it is sufficient to fasten the threads to the top sheet at the ends of the passages. Thus, when the nonwoven strips extend along the full length of the threads, it is sufficient to fasten the ends of the threads to the top sheet. The threads will preferably extend freely in these guide passages. The guide passages can be formed by folding the top sheet in conjunction with cutting-out the openings 15, 16, therewith forming the aforesaid nonwoven strips integrally with the top sheet.

The threads can also be fastened directly to the top sheet by the technique known from Swedish Patent Application No. 9304232-3 filed on the Dec. 21, 1993. This Application describes how elastic elements can be joined directly to an underlying substrate with the aid of thermoplastic components which are locked to the elastic elements by mechanical locking or chemical adhesion and which are joined to an underlying substrate, preferably by ultrasonic welding. The reader is referred to this last-mentioned Swedish patent application for a closer study in this regard.

A tubular body 26 is attached in a flattened state within the region 17 of the top sheet between the top sheet and the absorbent body, and extends transversely between the points at which the top sheet is fastened to the casing sheets 7 and 8. The upper and lower side of the tubular body 26 is attached respectively to the top sheet 9 and to the inner casing sheet 8 by means of a join which has a small extension in the longitudinal direction of the diaper, for instance by means of a glue bead.

FIG. 2 shows the diaper in a flat state, by which is meant the state in which the diaper is found during manufacture, the diaper in this state being held stretched against the spring force of the elastic devices mounted thereon. When the finished diaper is released, the elastic devices 10, 11, 24 and 25 endeavour to contract to a fully relaxed state and therewith bring the diaper to the shape shown in FIGS. 1 and 3.

The top sheet 9 is folded and shortened by contraction of the elastic threads 24, 25. Shortening of the top sheet is enabled by curving of the main body 2 of the absorbent body 1 at the same time as the side bodies 3, 4 swing upward about their respective hinges formed by the casing sheets 7, 8 joined in the gap between the side bodies 3, 4 and the main body 2 respectively. The top sheet 9 will thus be held distanced from the absorbent body 1 by virtue of the action of the elastic threads 24, 25.

Because the top side and the bottom side of the tubular body 26 are fastened respectively to the top sheet 9 and to the inner casing sheet 8 along a respective narrow string or strand 27 and 28, these parts of the tubular body will also be distanced from one another in a corresponding fashion. This means that the tubular body will be unfolded or raised from its flat state shown in FIG. 2. In the illustrated embodiment, the tubular body is so dimensioned that when the diaper has the configuration shown in FIGS. 1 and 3, the tubular body will have been raised so as to be practically almost flattened in the longitudinal symmetry plane of the diaper in a plane at right angles to said symmetry plane and to the absorbent body, as will best be seen from FIG. 3. The left part of FIG. 5 is a cross-sectional view of the diaper in the absence of load thereon. As will be seen from this Figure, raising of the tubular body 26 from its flattened state shown on the right of FIG. 5 and in FIG. 2 decreases successively in a direction towards the side edges of the diaper, i.e. to the left in the left-hand part of FIG. 5. The tubular body of this embodiment will thus have folds to an increasing extent towards the edges of the diaper. According to one variant, the tubular body can be given a circumference which decreases successively towards the side edges of the diaper from a central part delimited by the elastic threads 24, 25.

It is pointed out in this connection that FIG. 1 shows the diaper in the absence of load and not in its state when worn. The shape of the diaper when worn will naturally depend on the anatomy of the wearer and the diaper is so dimensioned as to cause the elastic threads 24, 25 to be slightly stretched when putting on the diaper. However, the length of the diaper is such that a large part of the folds or gathers will remain in the top sheet after putting on the diaper, so that the absorbent body will be spaced from the top sheet along a greater part of its extension, even when the diaper is in place on the wearer.

Thus, when the diaper is worn, there is located between the absorbent body and the top sheet a space in which urine and faeces can be held without coming into contact with the wearer's skin. It will be understood that the size and the positioning of the rear opening 15 is significant in ensuring that faeces discharged by the wearer will land in this space and not on the top sheet, particularly in respect of the faecal discharge point. It has been found that the distance between the side edges 18, 19 of the opening 15 should be at least 3 cm at the faecal discharge point, and that the front edge of the opening 15 should lie at least 1 cm, and preferably 2 cm, in front of the faecal discharge point, and that the front edge should have a length of at least 2 cm. Because the elastic threads 24, 25 exert a spring force in both the longitudinal and the transverse direction of the diaper, both the front edge and the side edges 18, 19 of the opening 15 are held stretched when the diaper is worn, so as to ensure that the aforesaid distance will be retained. In order to achieve a high stretching effect, the ends of the threads 24, 25 will preferably lie laterally on the level of the side edges of the absorbent body 1. The forward opening 16 in the top sheet 9 ensures that urine discharged by the wearer will fall directly onto the absorbent body and can therewith be absorbed immediately by said body.

The tubular body 26 forms a barrier which delimits the spaces beneath the openings 15, 16 from one another. This prevents urine and faeces mixing together, which would otherwise result in faecal enzymes splitting or cleaving urea in the urine, thereby forming ammonia. The formation of ammonia would result in an increase in pH, which in turn would result in increased activity of the enzymes protease and lipase in the faeces, giving rise to greater irritation of the skin should faeces come into contact therewith. The arrangement also ensures that faeces are unable to land in the space beneath the forward opening 16 and therewith come into contact with the genitals of the wearer.

In addition to gathering the top sheet 9, the elastic threads 24, 25 also lie against the wearer's body and therewith provide a sealing action. This greatly reduces the risk of urine discharged by male wearers landing on the top sheet and running along said sheet instead of passing down through the forward opening 16. Because the threads extend along the side edges of the openings 15, 16, the risk of the position of the openings 15, 16 changing due to external loads on the diaper, for instance caused by movement of the wearer, is also reduced at the same time. Another advantage is that if the absorbent body is pressed against the wearer's body by an externally acting load, it is more difficult for urine and faeces to leak over the edges of the openings 15, 16 and onto the top sheet 9 and there mixing together. It has been found that in order to achieve these sealing functions, the distance between the side edges 18, 19 of the rear opening 15 at the center of the faecal discharge point should not be greater than 6 cm and preferably less than 5 cm. The length of the front edge of the opening 15 should not exceed 4 cm.

From an absorption aspect, the side bodies 3, 4 are not joined to the remainder of the absorbent body 1 and form safety bodies which absorb liquid when the main absorbent body 2 becomes saturated or is unable to absorb the fluid discharged for some other reason. In addition to this function, the side bodies contribute towards the stability of the basin formed by contraction or gathering of the top sheet, and also prevent the whole of the main body from lying against the wearer's body when the diaper is subjected to an external load.

The tubular body 26 may be comprised of liquid-impermeable or liquid-permeable material, and the same material may be used as that from which the bottom sheet, the inner casing sheet or the top sheet are made.

Instead of a tubular body 26, which provides a two-wall barrier as shown in FIG. 3, it is possible to construct the barrier between the openings 15, 16 from one single wall of flexible material which is mounted between the inner casing sheet and the top sheet in a folded or pleated state, for instance in a bellows-like state, and fastened to said sheets in the same manner as the tubular body 26.

One such single-wall or sheet-like barrier 29 is shown in FIG. 6, which is a longitudinal sectional view corresponding to the view of FIG. 3 of a diaper comprising an absorbent body 30 enclosed between an outer and an inner casing sheet 31 and 32, and a top sheet 33 having a forward and a rearward opening 34 and 35 which are separated longitudinally by a top sheet region 36. The barrier 29 is comprised of a rectangular piece of liquid-impermeable or liquid-permeable material, which is disposed between the top sheet and the inner casing sheet in a single-fold in the same manner as that described earlier with reference to the tubular body 26. In this Figure, the raising or unfolding of the material piece 29 as a result of the top sheet being gathered in the vicinity of the side edges of the absorbent body and centrally between the side edges of the absorbent body is indicated in dotted and full lines respectively, while raising or unfolding of the material piece at a location between these positions is shown in broken lines.

It is also possible to form the barrier from folds in the inner casing sheet or in the top sheet as illustrated schematically in FIGS. 7–10, which illustrate center sections of the longitudinal sectional views corresponding to FIG. 6 of diapers constructed in the same manner as the diaper illustrated in FIG. 6.

The inner casing sheet shown in FIG. 7 includes two sheets 37, 38, of which the upper sheet 37 is folded and fastened to the bottom sheet 38 at least along two transversal joins 39, 40, which may consist of continuous or intermittent glue or weld joins and which are mutually spaced longitudinally. As will be seen from the Figure, which illustrates the configuration obtained when the top sheet is gathered or drawn together, the sheet 37 forms a U-shaped body between the joins, having two side walls 41, 42 and an upper wall 43 which is secured to the region 40' of the top sheet located between the openings therein, preferably by gluing.

The barrier 44 illustrated in FIG. 8 differs from the barrier 41–43 illustrated in FIG. 7 by virtue of the fact that the opposing parts of the fold formed in the inner casing sheet 45 have been mutually joined along the connections of the fold with the remainder of the casing sheet 45, so as to form a tubular body of triangular crosssection when the top sheet 46 is gathered or drawn together in that part of the fold which lies transversely central in and which is shown in this Figure.

FIGS. 9 and 10 illustrate a variant 47 of the fold 44 shown in FIG. 8, this variant differing from the fold 44 by virtue of the fact that the fold walls 48, 49 are glued together. FIG. 9 illustrates the configuration of the fold 47 in the manufacturing stage of the diaper, while FIG. 10 illustrates the fold 47 subsequent to gathering of the diaper top sheet. The fold is glued or welded to that region 50 of the top sheet which lies between the top sheet openings.

Naturally, a barrier forming fold can be provided in the top sheet instead of in the inner casing sheet, similar to the manner shown in FIGS. 8–10.

It will be understood that the described embodiment of the invention can be modified within the scope of the invention. For instance, the shapes and dimensions of the openings in the top sheet can be varied, particularly with regard to the position of the mutually distal edges of the openings. The invention can, of course, be applied with diapers whose absorbent body has a different construction and shape to that described, for instance rectangular absorbent bodies comprising one or more absorbent layers. The invention can also be applied, of course, with so-called pant diapers, or training pants, and with incontinence guards. The invention is therefore limited solely by the content of the following Claims.

We claim:

1. An absorbent article comprising:
   front and rear parts and a crotch part therebetween;
   an absorbent body extended longitudinally from said front part to said rear part;
   a liquid-impermeable bottom sheet and a liquid-permeable casing sheet sandwiching said absorbent body;
   a monolithic top sheet that lies proximal to a wearer's body when the article is being worn, said top sheet having a first opening therethrough at said front part and a second opening therethrough at said rear part, said first and second openings each having longitudinal edges and respective front and rear part lateral edges spaced from peripheral edges of said top sheet and crotch part lateral edges separated from each other by a laterally extended bridge of said top sheet,
   said longitudinal edges of each of said first and second openings converging continuously from a respective one of said front and rear part lateral edges to a respective one of said crotch part lateral edges to provide each of said openings with a truncated triangular shape when said top sheet is flat;
   said top sheet being directly connected to said casing sheet at a periphery of said top sheet;
   elastic devices fastened to said top sheet in the stretched state that separate said top sheet from said casing sheet when contracted, except at said periphery of said top sheet; and
   a laterally aligned flexible member directly connected to said top sheet across said bridge and that is either directly connected to or is part of said casing sheet adjacent said crotch part, said flexible member being a side of a first pouch that opens at said first opening and a side of a second pouch that opens at said second opening and separates said first and second pouches from each other.

2. The absorbent article of claim 1, wherein said flexible member comprises a tubular body having diametrically opposing sides affixed to said bridge of said top sheet and to said casing sheet, respectively.

3. The absorbent article of claim 1, wherein said flexible member comprises a fold of said casing sheet that is affixed to said bridge of said top sheet.

4. The absorbent article of claim 1, wherein said flexible member comprises a single sheet affixed to said bridge of said top sheet and to said casing sheet.

5. The absorbent article of claim 1, wherein said first opening is for being positioned adjacent a wetting point of the wearer and said second opening is for being positioned adjacent a faecal discharge point of the wearer, when the article is being worn.

6. The absorbent article of claim 1, wherein said respective front and rear part lateral edges of said first and second openings each are curved away from longitudinal ends of said front and rear parts.

7. The absorbent article of claim 1, wherein said elastic devices are fastened to said longitudinal edges of said first and second openings.

8. The absorbent article of claim 1, wherein said absorbent body comprises a longitudinally extended central body and two side bodies laterally separated from each other.

9. The absorbent article of claim 8, wherein said casing sheet is affixed to said bottom sheet at separations between said side bodies and said central body.

10. The absorbent article of claim 1, wherein said front and rear part lateral edges of said first and second openings are spaced farther from longitudinal ends of the front and rear parts, respectively, than corresponding ends of said absorbent body.

* * * * *